(12) United States Patent
Moszner et al.

(10) Patent No.: US 7,927,538 B2
(45) Date of Patent: Apr. 19, 2011

(54) LIGHT-CURING SLIPS FOR THE STEREOLITHOGRAPHIC PREPARATION OF DENTAL CERAMICS

(75) Inventors: Norbert Moszner, Triesen (LI); Wolfgang Wachter, Schaan (LI); Christoph Appert, Vaduz (LI); Volker M. Rheinberger, Vaduz (LI); Robert Liska, Schleinbach (AT); Jurgen Stampfl, Vienna (AT); Johannes Patzer, Vienna (AT)

(73) Assignees: Ivoclar Vivadent AG, Schaan (LI); Technische Universitat Wien, Vienna (AT)

( * ) Notice: Subject to any disclaimer, the term of this patent is extended or adjusted under 35 U.S.C. 154(b) by 0 days.

(21) Appl. No.: 12/394,452

(22) Filed: Feb. 27, 2009

(65) Prior Publication Data

US 2010/0029801 A1 Feb. 4, 2010

(30) Foreign Application Priority Data

Jul. 30, 2008 (EP) .................................... 08161505

(51) Int. Cl.
- *A61K 6/00* (2006.01)
- *A61C 5/00* (2006.01)
- *C08K 9/00* (2006.01)
- *C08K 3/22* (2006.01)
- *G03F 7/00* (2006.01)
- *B29C 35/04* (2006.01)

(52) U.S. Cl. ............... 264/401; 522/77; 522/79; 522/81; 522/180; 522/76; 523/113; 523/115; 430/269; 433/218; 433/222.1; 433/213; 433/228.1

(58) Field of Classification Search .................. 264/401; 430/269; 522/83, 81, 76–79; 433/222.1, 433/228.1, 218, 213; 523/115, 116–117, 523/113
See application file for complete search history.

(56) References Cited

U.S. PATENT DOCUMENTS

| | | | |
|---|---|---|---|
| 4,437,836 A * | 3/1984 | Schmitz-Josten et al. | 433/199.1 |
| 4,778,834 A * | 10/1988 | Murray | 523/212 |
| 5,380,179 A * | 1/1995 | Nishimura et al. | 419/36 |
| 5,496,682 A * | 3/1996 | Quadir et al. | 430/269 |
| 5,768,134 A | 6/1998 | Swaelens et al. | |
| 5,877,232 A | 3/1999 | Storch et al. | |
| 6,096,903 A | 8/2000 | Moszner et al. | |
| 6,117,612 A | 9/2000 | Halloran et al. | |
| 6,245,828 B1 | 6/2001 | Weinmann et al. | |
| 6,376,585 B1 * | 4/2002 | Schofalvi et al. | 524/195 |
| 6,387,981 B1 * | 5/2002 | Zhang et al. | 523/117 |
| 6,465,541 B2 * | 10/2002 | Bretscher et al. | 523/117 |
| 6,632,853 B2 * | 10/2003 | Alkemper et al. | 522/83 |
| 6,811,937 B2 * | 11/2004 | Lawton | 430/15 |
| 6,890,968 B2 * | 5/2005 | Angeletakis et al. | 523/115 |
| 6,939,489 B2 | 9/2005 | Moszner et al. | |
| 6,977,095 B1 * | 12/2005 | Marx et al. | 427/2.26 |
| 2005/0090575 A1 * | 4/2005 | Chaput et al. | 523/115 |
| 2006/0247329 A1 | 11/2006 | Moszner et al. | |

FOREIGN PATENT DOCUMENTS

| | | |
|---|---|---|
| CA | 2 295 896 C | 7/2000 |
| DE | 199 38 463 A1 | 2/2001 |
| DE | 199 50 284 A1 | 4/2001 |
| DE | 10 2005 058 116 A1 | 3/2007 |
| WO | 97/29901 A1 | 8/1997 |

OTHER PUBLICATIONS

Beil et al., Fertigung von Mikro-Bauteilen mittels Stereolithographie, Dusseldorf:VDI Verlog GmbH, pp. 3-31 and 40-61 (2002).
Dietliker et al., "Photolatent Tertiary Amines—A New Technology Platform for Radiation Curing," Chimia 61:655-660 (2007).
Elias, Makromolekule, vol. 1, 6th Ed., Weinheim:Wiley-VCH, pp. 193-197 (1999).
Fouassier, eds., Radiation Curing in Polymer Science and Technology, vol. II, London and New York:Elsevier Applied Science (1993).
Gebhardt, Generative Fertigungsverfahren, 3rd Ed., Munich:Carl Hanser, pp. 77 et seq. (2007).
Gebhardt, "Vision Rapid Prototyping," Ber DGK 83(13):7-12 (2006).
Moreno, "The Role of Slip Additives in Tape Casting Technology: Part II-Binders and Plasticizers," Amer. Ceram. Soc. Bull. 71:1647-1657 (1992).
Otsu, "Role of Initiator-Transfer Agent-Terminator (Iniferter) in Radical Polymerizations: Polymer Design by Organic Disulfides as Iniferters," Makromol. Chem. Rapid Commun. 3:127-132 (1982).

\* cited by examiner

*Primary Examiner* — Susan W Berman
(74) *Attorney, Agent, or Firm* — Ann M. Knab

(57) ABSTRACT

Slip based on a polyreactive binder, polymerization initiator and filler, which contains (A) 5-65 wt.-% polymerizable binder, (B) 0.001-1.0 wt.-% photoinitiator and (C) 35-90 wt.-% surface-modified ceramic and/or glass ceramic particles relative to the overall mass of the slip, and process for the preparation of ceramic mouldings by rapid prototyping processes using the slip.

57 Claims, 1 Drawing Sheet

LIGHT-CURING SLIPS FOR THE STEREOLITHOGRAPHIC PREPARATION OF DENTAL CERAMICS

This application claims the benefit of European Patent Application Serial No. 08161505.6, filed Jul. 30, 2008, which is hereby incorporated by reference in its entirety.

FIELD

The present invention relates to light-curing slips for the stereolithographic preparation of ceramic mouldings, e.g. dental inlays, onlays, veneers, crowns, bridges and frameworks.

BACKGROUND

The term "rapid prototyping" (RP) covers generative manufacturing processes in which 3-dimensional models or components are prepared from computer-aided design data (CAD data) (A. Gebhardt, Vision of Rapid Prototyping, Ber. DGK 83 (2006) 7-12). These are processes such as e.g. stereolithography (SL), selective laser sintering (SLS), 3-D printing, fused deposition modelling (FDM), ink-jet printing (IJP), 3D plotting, multi-jet modelling (MJM), solid freeform fabrication (SFF), laminated object manufacturing (LOM), laser powder forming (LPF) and direct ceramic jet printing (DCJP), with which models, components or spacers can be prepared cheaply even on a small scale (A. Gebhardt, Generative Fertigungsverfahren, 3$^{rd}$ ed., Carl Hanser Verlag, Munich 2007, 77 et seq.). Stereolithography involves RP processes (A. Beil, Fertigung von Mikro-Bauteilen mittels Stereolithographie, Düsseldorf 2002, VDI-Verlag 3 et seq.) in which a spacer is constructed in layers from a liquid and curable monomer resin on the basis of CAD data.

Stereolithographic processes for the preparation of dental mouldings such as inlays, crowns or bridges are highly advantageous particularly with ceramic materials because the impression-taking and casting processes and the grinding and milling operations respectively, which involve considerable manual outlay in the dental engineering laboratory, can thus be greatly simplified and at the same time the large material loss which occurs with non-generative processes can be avoided. As a complete digital process chain is in place today, the standard process steps for the preparation of e.g. multi-unit bridge frameworks (alignment in the articulator, wax modulation, embedding and casting) can be replaced by the digitalization of the model, virtual design of the dental spacer and its generative stereolithographic manufacture.

In the stereolithographic preparation of ceramic spacers a ceramic green compact is firstly prepared by layered radiation curing of a free-flowing ceramic slip which is then sintered after debinding to form a dense ceramic moulding. The green compact is also called a green body. The term debinding is used to describe the elimination of the binder. Here, the binder used is usually removed by heating the green compact to a temperature of approx. 90° C. to 600° C. It is essential that the formation of cracks and deformations is very largely avoided. The green compact becomes the so-called white body as a result of the debinding.

In debinding, purely thermal and thermochemical processes take place. Mixtures of water, solvents, polymers, waxes or oils are usually used as binders in the pressing of ceramic powders. Polypropylene, polyethylene, polyvinyl acetate, polyvinyl alcohol, methylcellulose, polyvinylpyrrolidone, polystyrene or polyethyl methacrylate are mostly used as polymers (cf. R. Moreno, Amer. Cer. Soc. Bull. 71 (1992) 1647-1657). These are linear polymers which are broken down more or less easily into volatile components by depolymerization or chain-splitting at increased temperature.

In the case of green bodies produced by stereolithography based on cross-linking monomer mixtures, there is a polymer network. Through the use of cross-linking monomers the curing time which is required to obtain a stable solid can be significantly shortened, but at the same time the polymer network that forms also displays a much higher thermal stability compared with linear polymers, which adversely affects the debinding process.

The sintering of the white body takes place in the sintering furnace during high-temperature firing. The finely-dispersed ceramic powder is compacted and solidified by exposure to temperature below the melting temperature of the main component, as a result of which the porous component becomes smaller and its strength increases.

EP 1 021 997 A2 describes the use of the laser-sintering process for the preparation of dental restorations. Here, metal powders are sintered in layers using a laser.

DE 101 14 290 A1 relates to the preparation of dental spacers by 3-D plotting using materials that are meltable, condensable, curable thermally or with UV or visible light, filled or unfilled. Proposed for the preparation of green bodies are inorganic pastes which are composed of glass, glass ceramic or ceramic powder, which is converted into a shapable paste with solvent, binder and plasticizer. The powders used are not surface-modified.

WO 97/29901 describes a process and an apparatus for the preparation of 3-dimensional components of a liquid, curable medium. The component is constructed in layers by scanning each individual layer with a laser and curing it. The next layer of the curable material is then deposited by means of a coating device and then likewise cured.

A stereolithographic process for the preparation of dental implants is known from WO 95/28688.

U.S. Pat. No. 5,496,682 discloses light-curable compositions for the preparation of three-dimensional bodies by stereolithography, which contain 40 to 70 vol.-% ceramic or metal particles, 10 to 35 wt.-% monomer, 1 to 10 wt.-% photoinitiator, 1 to 10 wt.-% dispersant and preferably also solvent, plasticizer and coupling agent.

U.S. Pat. No. 6,117,612 discloses resins for the stereolithographic preparation of sintered ceramic or metal parts. The resins have a viscosity of less than 3000 mPa·s. For their preparation, monomers with a low viscosity are used, preferably in aqueous solution. A high solids content and low viscosity are said to be achieved through the use of dispersants.

DE 10 2005 058 116 A1 discloses suspensions for the stereolithographic preparation of ceramic implants in the manner described in U.S. Pat. No. 6,117,612, which do not contain diluents such as water or organic solvents, as the latter are said to increase the viscosity through local evaporation when energy is introduced. The viscosity of the suspension is set at less than 20 Pa·s by varying the concentration of a dispersant. Alkyl ammonium salts of copolymers with acid groups are used as dispersants, wherein the latter can also be coated onto the particles of the ceramic powder.

Methods and compositions for the stereolithographic preparation of ceramic components are described in US 2005/0090575 A1. It is stated that spacers prepared with the liquid materials known from U.S. Pat. No. 5,496,682 are soft and therefore require an additional curing step in order to avoid deformations during firing, while mouldings obtained from paste-like materials form internal stresses during debinding which lead to cracks during sintering. To avoid these problems, plasticizers are used and the quantity of ceramic powder chosen such that the viscosity of the compositions is at least 10,000 Pa·s.

Compositions curable with visible light and their use for the preparation of dental restorations from plastic materials with RP processes are described in DE 199 38 463 A1 and DE 199 50 284 A1.

In RP processes, the composition and the properties of the radiation-curable slip are of decisive importance. Thus as high as possible a volume fraction of the ceramic particles in the slip is required in particular for a high density and final strength as well as good accuracy of fit of the ceramic spacer. Furthermore, a well-set rheology of the slip is a basic requirement for the stereolithographic construction of a defect-free green body, wherein the viscosity and the flow behaviour depend among other things on the size and the content of the ceramic particles in the slip. It is also to be borne in mind that the binder can be removed residue-free without the formation of cracks or stresses during the debinding of the green body.

It is furthermore important that the slips used for the preparation of the green compacts are storage-stable over a sufficient period of time and are largely inert vis-à-vis the tank material, the base surface and the other components with which it comes into contact in the course of the stereolithography process.

A particular problem in the preparation of ceramic spacers by RP processes is the colouring of the ceramic, as the colorants used must survive the debinding and sintering process.

The known slips are not satisfactory in respect of the abovenamed requirements. The object of the invention is therefore to provide improved light-curing slips for the stereolithographic preparation of ceramic and glass ceramic spacers which satisfy the above requirements. The slips are intended to produce green compacts with sufficient strength which can be debound without deformation, the formation of cracks or stresses and which produce upon sintering high-strength ceramics which are suitable for dental purposes. According to a preferred embodiment, the ceramics are to have a colouring adapted to the desired intended use.

SUMMARY

This object is achieved according to the invention by slips based on radically polymerizable binders, polymerization initiators and fillers which contain (A) 5-65 wt.-%, preferably 9 to 65 wt.-%, particularly preferably 10 to 40 wt.-% polyreactive binder,
(B) 0.001 to 1.0 wt.-%, preferably 0.01 to 1.0 wt.-%, particularly preferably 0.1 to 1.0 wt.-% photoinitiator and
(C) 35-90 wt.-%, preferably 50 to 90 wt.-%, particularly preferably 60 to 90 wt.-% surface-modified ceramic and/or glass ceramic particles, in each case relative to the overall mass of the slip.

DETAILED DESCRIPTION

Figure 1:
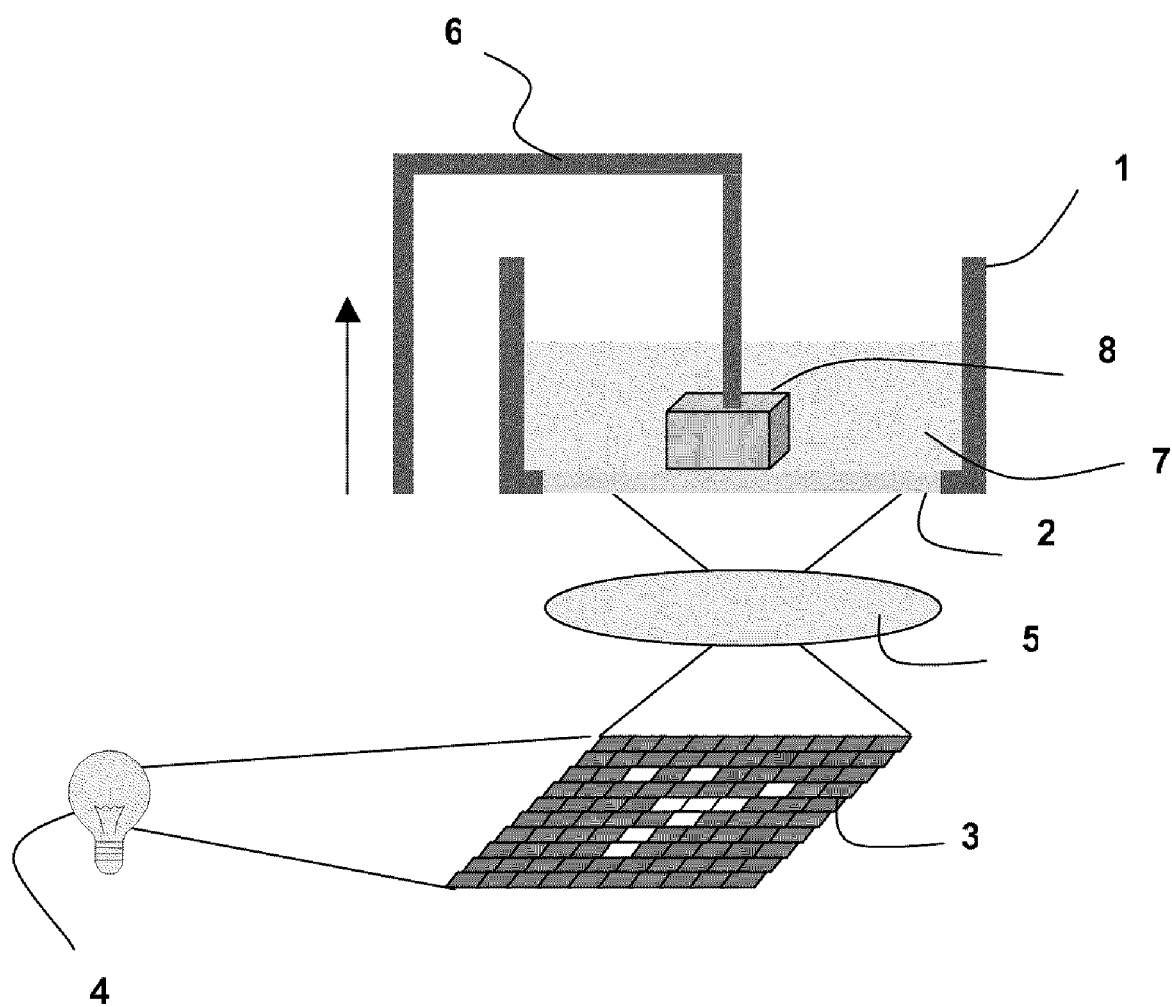
FIG. 1 shows a schematic representation of a device for carrying out the process according to the invention.

In particular polymerization and polyaddition resins which as a rule are composed of a mixture of low-molecular or oligomeric monomers which contain one or more polyreactive groups can be used as polyreactive binder A.

In the case of polymerization resins, radically and cationically polymerizable resins and monomers are preferably used for ring-opening metathesis polymerization. In the case of the polyaddition resins, thiol-ene resins and Michael reaction resins are above all suitable.

In particular mono- or multifunctional (meth)acrylates or their mixtures can in particular be used as radical polymerization resins. Preferred monomers are acrylates such as hydroxyethyl, hydroxypropyl, benzyl, tetrahydrofurfuryl or isobornyl acrylate, and also di-, tri- or tetraethylene glycol diacrylate, acrylate-group-terminated poly(ethylene glycol)s and poly(propylene glycol)s, hexanediol diacrylate, trimethylolpropane triacrylate and pentaerythritol tetraacrylate. Di- or multifunctional acrylates are preferably used mixed with monoacrylates in the organic suspension.

According to the invention, acrylates are preferred due to their higher reactivity compared with the corresponding methacrylates, which manifests itself in a swifter curing. As organic components are removed during debinding, the use of acrylates is harmless from a toxicological view, with the result that the reactivity advantages of the acrylates can be used.

Further preferred monomers are acrylamides such as N-ethylacrylamide, N,N-dimethylacrylamide, N-(2-hydroxyethyl)acrylamide, N,N'-diethyl-1,3-bis(acrylamido)-propane and 1,4-bis(acrylamido)-butane. The bisacrylamides are preferably used in excess compared with the monoacrylamides in the organic binder. The proportion of monoacrylamides in component (A) is preferably 30 wt.-% or less.

The properties of the slips before and after the light-curing can be influenced by a targeted combination of monomers. Mixtures of monofunctional and difunctional monomers are characterized by a relatively low viscosity and reactivity of the resin mixture, wherein viscosity and reactivity decrease with the monofunctional monomers content. A monofunctional monomers content ensures a lower brittleness and a swifter debinding of the green compacts obtained by light-curing of slips. Mixtures of difunctional and trifunctional monomers have a higher viscosity and reactivity, wherein viscosity and reactivity increase with the trifunctional monomers content. The trifunctional monomers content effects a higher brittleness and slower debinding of the green compacts. Reactivity and viscosity of the resin mixture and also the polymerization shrinkage are furthermore determined by the molar mass of the monomers, wherein the reactivity and polymerization shrinkage decrease with increasing molar mass, while the viscosity increases. Finally, the polarity of the monomers can be used to influence the interaction with the material of the stereolithographic tank, such as e.g. the swelling of the material of the polymerization tank. Silicone elastomers are often used as tank materials. Through the use of OH-group-containing monomers, a swelling of silicone elastomers can largely be avoided.

Cationically ring-opening polymerizable monomers such as e.g. glycidyl ether or cycloaliphatic epoxides, cyclic ketene acetals, spiroorthocarbonates, oxetanes or bicyclic orthoesters can be used as cationic polymerization resins. Preferred examples are: 2-methylene-1,4,6-trioxaspiro[2.2]-nonane, 3,9-dimethylene-1,5,7,11-tetraoxaspiro[5.5]undecane, 2-methylene-1,3-dioxepane, 2-phenyl-4-methylene-1,3-dioxolane, bisphenol-A-diglycidyl ether, 3,4-epoxycyclohexylmethyl-3,4-epoxycyclohexancarboxylate, bis(3,4-epoxycyclohexylmethyl)adipate, vinylcyclohexene dioxide, 3-ethyl-3-hydroxymethyloxetane, 1,10-decandiyl-bis-(oxymethylene)-bis-(3-ethyloxetane) or 3,3-(4-xylylenedioxy)-bis-(methyl-3-ethyloxetane) and the epoxides named in EP 0 879 257 B1. Preferred monomers are bisphenol-A-diglycidyl ether, 3,4-epoxy-cyclohexylmethyl-3,4-epoxycyclohexancarboxylate and bis(3,4-epoxycyclohexylmethyl)adipate.

Silicic acid polycondensates which carry cationically polymerizable groups, preferably epoxide, oxetane, or spiro-orthoester groups, and which are accessible for example by hydrolytic condensation of silanes are also suitable as cationically polymerizable matrix systems. Such silicic acid polycondensates are described for example in DE 41 33 494 C2 and U.S. Pat. No. 6,096,903, which are hereby incorporated by reference in their entirety. Preferred silicic acid polycondensates are those which are obtained by hydrolytic homo- or cocondensation of 2-(3,4-epoxycyclohexyltrimethoxysilane and/or -triethoxysilane. Furthermore vinyl ethers such as e.g. ethyl or isobutyl vinyl ether, and also N-vinylpyrrolidone can also be used as cationically polymerizable monomers.

Moreover, mixtures of radically and cationically polymerizable monomers can also be used.

Known RÖMP monomers, such as monocyclic alkenes or alkadienes, for example cyclopentene, cycloheptene, cyclooctene, cyclododecene or 1,5-cyclooctadiene, or bicyclic alkenes, for example bicyclo[2.2.1]hept-2-ene (2-norbornene) or derivatives derived therefrom, such as 7-oxa-bicyclo[2.2.1]hept-2-ene, bicyclo[2.2.1]hept-5-ene-2,3-dicarboxylic acid dimethyl ester, 7-oxabicyclo[2.2.1]hept-5-ene-2,3-diethyl ester, 5-norbornene-2-methyl ester or 5-norbornene-2-yl-esters of mono-, di- and polycarboxylic acids or the conversion products of 5-norbornene-2-methanol or 5-norbornene-2-ol with mono- or diisocyanates can be used as monomers for ring-opening metathesis polymerization (RÖMP). The RÖMP monomers can also be used e.g. in mixture with radically polymerizable monomers, in particular with mono- or multifunctional (meth)acrylates.

Thiol-ene resins which consist of mixtures of mono- or multifunctional mercapto compounds and di- or multifunctional unsaturated monomers, in particular allyl or norbornene compounds, are particularly suitable as polyreactive binder A. Examples of mono- or multifunctional mercapto compounds are o-, m- or p-dimercaptobenzene and esters of thioglycol or of 3-mercaptopropionic acid of ethylene, propylene or butylene glycol, hexanediol, glycerol, trimethylolpropane or pentaerythritol. Examples of di- or multifunctional allyl compounds are esters of allyl alcohol with di- or tricarboxylic acids, such as malonic, maleic, glutaric, succinic, adipic, sebacic, phthalic, terephthalic or gallic acid and mono- or trifunctional allyl ethers, such as e.g. diallyl ether, $\alpha,\omega$-bis[allyloxy]alkanes, resorcinol or hydroquinone diallyl ether and pyrogallol triallyl ether, or other unsaturated compounds such as e.g. 1,3,5-triallyl-1,3,5-triazine-2,4,6-(1H,3H,5H)-trione, tetraallylsilane or tetraallylorthosilicate. Examples of di- or multifunctional norbornene compounds are Diels-Alder addition products of cyclopentadiene or furan with di- or multifunctional (meth)acrylates, and esters and urethanes of 5-norbornene-2-methanol or 5-norbornene-2-ol with di- or polycarboxylic acids such as e.g. malonic, maleic, glutaric, succinic, adipic, sebacic, phthalic, terephthalic or gallic acid, with di- or polyisocyanates, such as hexamethylene diisocyanate or its cyclic trimer, 2,2,4-trimethylhexamethylene diisocyanate, toluylene diisocyanate or isophorone diisocyanate. Thiol-ene resins are advantageously characterized by a low viscosity and a low polymerization shrinkage. Moreover, the mercapto groups of the thiol component result in an interaction with the surface of the ceramic particles and thus stabilize the slip.

Particularly preferred thiol-ene components are mixtures of esters of 3-mercaptopropionic acid with hexanediol, glycerol, trimethylolpropane and/or pentaerythritol with one or more of the following-ene components: bicyclo[2.2.1]hept-2-ene, bicyclo[2.2.1]hept-5-ene-2,3-dicarboxylic acid dimethyl ester, 7-oxa-bicyclo[2.2.1]hept-5-ene-2,3-dicarboxylic acid diethyl ester, 5-norbornene-2-methyl ester of succinic acid or adipic acid and also esters of allyl alcohol with adipic, terephthalic or gallic acid, hydroquinone diallyl ether, pyrogallol triallyl ether and 1,3,5-triallyl-1,3,5-triazine-2,4,6-(1H,3H,5H)-trione.

So-called Michael reaction resins can also be used as polyreactive binder. These are preferably mixtures of acylamides and/or bisacrylamides, in particular di- and/or multifunctional acrylates with di- or multifunctional acetoacetates. Examples of suitable acrylates are ethylene glycol diacrylate, hexanediol diacrylate, tripropylene glycol diacrylate, ethoxylated bisphenol-A-diacrylate, polyethylene glycol-200-diacrylate, trimethylolpropanetriacrylate, pentaerythritol tetraacrylate. These acrylates can be converted into network polymers in particular with di-, tri- or tetrafunctional acetoacetates, such as e.g. hexanediol diacetoacetate, trimethylolpropane and glycerol trisacetoacetate and also pentaerythritol tetrakis acetoacetate. The formation of suitable catalysts and thus the Michael reaction between the di- or multifunctional acrylates with the di- or multifunctional acetoacetates can be photochemically induced. Strong bases such as e.g. 1,5-diazabicyclo[4.3.0]non-5-ene (DBN) which can be released from corresponding precursors by irradiation with light are particularly suitable as catalysts for the Michael reaction. The photo-induced release of DBN from N-benzylated precursors is described e.g. in: K. Dietliker, T. Jung, K. Studer, J. Benkhoff, *Chimia* (2007) 655-660, which is hereby incorporated by reference in its entirety. Further so-called photolatent bases are described below.

If the acrylates are added in excess or the acetoacetates contain polymerizable groups, such as 2-acetoacetoxyethyl methacrylate, or if the acrylates are dissolved in a mono- or dimethacrylate or their mixtures, a radical polymer network can also be formed at the same time with the formation of a polyaddition network. The elasticity, strength of the addition polymer matrix and its decomposition in the debinding process can be varied in targeted manner through the structure and functionality of the acetoacetates and acrylates. Thus difunctional components are particularly preferred which, compared with tri- or tetrafunctional components, result in a relatively low cross-linking density and therefore better debindability. The flexibility of the polymer matrix can be influenced through the choice of spacer groups. By spacer groups—also called spacers—are meant radicals which connect together two or more functional groups such as e.g. acetoacetate or acrylate groups. For example, longer and/or non-polar spacer groups, such as e.g. decamethylene groups, give a higher flexibility compared with propylene- or methyleneoxymethylene spacers.

According to the invention, mixtures are preferably used which contain less than 20 wt.-% monoacrylates and monoacetoacetates.

The choice of photoinitiator B depends on the type of monomer used. Slips based on radically-polymerizable resins and thiol-ene polyaddition resins can be polymerized with the known radical photoinitiators for the visible range (cf. J. P. Fouassier, J. F. Rabek (eds.), *Radiation Curing in Polymer Science and Technology*, Vol. II, Elsevier Applied Science, London and New York (1993), which is hereby incorporated by reference in its entirety), such as e.g. acyl or bisacylphosphine oxides, preferably with $\alpha$-diketones such as 9,10-phenanthraquinone, diacetyl, furil, anisil, 4,4'-dichlorobenzil and 4,4'-dialkoxybenzil, and particularly preferably camphorquinone. To accelerate the initiation $\alpha$-diketones are preferably used in combination with aromatic amines. Redox systems which have proved particularly worthwhile are combinations of camphorquinone with amines such as N,N-dimethyl-p-toluidine, N,N-dihydroxyethyl-p-toluidine, 4-dimethylaminobenzoate or structurally related systems.

Particularly preferred photoinitiators are Norrish type I photoinitiators, in particular monoacyltrialkyl- or diacyldialkylgermanium compounds, such as e.g. benzoyltrimethylgermanium, dibenzoyldiethylgermanium or bis(4-methoxybenzoyl)diethylgermanium. Mixtures of the different photoinitiators can also be used, such as e.g. dibenzoyldiethylgermanium combined with camphorquinone and 4-dimethylaminobenzoate.

To avoid the polymerization of monomer portions which have dissolved or embedded themselves in the material of the stereolithographic tank, it is particularly advantageous to use photoinitiators and accelerators which are characterized by a low solubility in the tank material. The polymerization is thereby prevented from resulting in a bond between the tank and the stereolithographically produced layer. Such a bond would mean that when the substrate carrier is raised to produce the next layer, either the component would be torn from the platform and/or the tank damaged. If an initiator which does not dissolve in the tank material is used, no polymerization can take place there.

Commercially available tanks are often composed of hydrophobic silicone elastomer (polysiloxane). In this case, in particular polar or hydrophilic photoinitiators and accelerators are advantageous. The polarity or hydrophilia of the photoinitiators and accelerators can be increased by the incorporation of corresponding functional groups, such as e.g. OH or ionic groups or polar radicals, such as e.g. di- or triethylene glycol radicals.

Also advantageous are oligomeric or polymeric photoinitiators and accelerators such as e.g. oligomers or polymers of the polymerizable photoinitiator 10-methacryloyloxycamphorquinone or the polymerizable accelerator 2-(dimethylamino)ethyl methacrylate which can enter the tank material only with difficulty due to their high molecular weight. Polymeric photoinitiators and accelerators can also be obtained by thermally copolymerizing polymerizable initiators or accelerators with polar comonomers, such as e.g. 2-hydroxyethyl methacrylate, or non-polar comonomers such as e.g. styrene. In this way, the polarity and the molar mass can be set in a targeted manner and thus the solubility of the photoinitiators and/or accelerators in the material of the stereolithographic tank or other materials effectively reduced.

Slips according to the invention based on cationically polymerizable resins can be cured with the known cationic photoinitiators, in particular with diaryliodonium or triarylsulphonium salts, optionally in the presence of suitable sensitizers, such as e.g. camphorquinone, monoacyltrialkyl- or diacyldialkylgermanium compounds, such as e.g. benzoyltrimethylgermanium, dibenzoyldiethylgermanium or bis(4-methoxybenzoyl)diethylgermanium. Examples of suitable diaryliodonium salts which can be used with camphorquinone, monoacyltrialkyl- or diacyldialkylgermanium compounds or thioxanthonene as sensitizers in the visible range are the commercially available 4-octyloxyphenyl-phenyl-iodonium hexafluoroantimonate or isopropylphenyl-methylphenyl-iodonium tetrakis(pentafluorophenyl)borate.

Suitable for the initiation of the ring-opening metathesis polymerization induced with visible light of slips based on RÖMP monomers are in particular ruthenium complexes which carry an N-heterocyclic carbene ligand, preferably ruthenium complexes according to the following formula, wherein $R_1$ and $R_2$ represent alkyl groups, in particular methyl, and $R_2$ can also be phenyl, halogen or alkoxy:

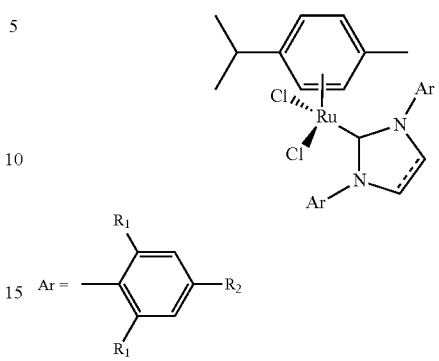

So-called photolatent bases can be used to trigger the light-induced Michael addition of slips based on Michael reaction resins. These are compounds which form catalytically active tertiary amine components upon irradiation of light. Examples of this are photolatent amidines, such as e.g. 5-benzyl-1,5-diazabicyclo[4.3.0]non-5-ene which forms 1,5-diazabicyclo[4.3.0]-5-nonene upon irradiation, which is a very effective catalyst for the Michael reaction of acetoacetates with acrylates. Photolatent bases can also be combined with known sensitizers for the visible range. α-diketones, such as 9,10-phenanthraquinone, diacetyl or in particular camphorquinone are preferred as photosensitizers.

As component C, the slips according to the invention contain surface-modified ceramic and/or glass ceramic particles.

By ceramics are meant inorganic materials which have a crystalline structure and are usually prepared from corresponding powders. The preparation of the ceramic usually takes place by sintering (sintered ceramic). Oxide ceramics are preferably obtained by sintering metal oxide powders such as e.g. $ZrO_2$ or $Al_2O_3$. In addition, oxide ceramics can also contain one or more glass phases. Glass ceramics are materials which are usually prepared from amorphous glasses, in particular silicate glasses, by controlled crystallization and in which a glass phase and one or more crystal phases are present simultaneously in the solid. In the case of sinterable glass ceramics, both glass powders and glass ceramic powders can be used as a starting point.

Preferred sinterable glass ceramic particles are based on leucite- or lithium-disilicate-reinforced glasses and/or ceramic particles based on $ZrO_2$ or $Al_2O_3$, preferably pure $ZrO_2$ or pure $Al_2O_3$, particles based on $ZrO_2$ stabilized with $HfO_2$, CaO, $Y_2O_3$, $CeO_2$ and/or MgO, particles based on other metal oxides and also ceramic composite materials which are prepared from several oxides and are thus constructed from various crystalline oxide phases, preferably $ZrO_2$—$Al_2O_3$, in particular pure $ZrO_2$—$Al_2O_3$ or $ZrO_2$—$Al_2O_3$ stabilized with $HfO_2$, CaO, $Y_2O_3$, $CeO_2$ and/or MgO.

The term "pure" is to be understood in the sense of "chemically pure", i.e. a $ZrO_2$ or $Al_2O_3$ ceramic is constructed only from $ZrO_2$ or $Al_2O_3$. In addition to the base oxide such as $ZrO_2$ or $Al_2O_3$, stabilized ceramics contain a stabilizer which is preferably selected from $HfO_2$, CaO, $Y_2O_3$, $CeO_2$, MgO and mixtures thereof The stabilizer is preferably used in a quantity from 3 to 5 wt.-% relative to the mass of the stabilized ceramic. High-strength $ZrO_2$ ceramics preferably contain 3 to 5 wt.-% $Y_2O_3$ (yttrium oxide) to stabilize the tetragonal crystal structure. This $ZrO_2$ ceramic is called Y-TZP (yttrium-stabilized tetragonal zirconium dioxide polycrystals). Ceramic particles which contain only base oxide and stabilizer are particularly preferred.

The particle size of component B is preferably in the range from 50 nm to 50 μm. It depends on the ceramic used. In the case of $Al_2O_3$, the size of the particles used as component B is preferably in the range from 50 to 500 nm, particularly preferably between 75 and 200 nm; in the case of glass ceramic in the range of 500 nm and 50 μm, quite preferably between 1 and 10 μm; in the case of TZP-3Y zirconium dioxide in the range between 50 and 500 nm, quite preferably between 50 and 350 nm. The particle size is preferably chosen such that sedimentation-stable slips are obtained. The particle sizes are the absolute upper and lower limits.

Furthermore, ceramic or glass ceramic particles with a particle size in the range from 10-200 nm can also be used as nano- or organosols, i.e. as a dispersion of the nanoparticles in a solvent, a suitable monomer of component A or a mixture thereof.

The particles are surface-modified with suitable substances. Compounds which are chemically bound, i.e. by ionic or covalent bonds, to the surface of the ceramic or glass ceramic particles are preferably used for the surface modification. Compounds which contain either acid groups, preferably carboxylic acid, phosphonic acid, hydrogen phosphate groups or acid phosphoric acid ester groups, or silyl groups, preferably alkoxysilyl groups, are preferred. The particle surface can be partially or preferably completely covered with the modification agent. The modification agents used according to the invention are monomeric compounds.

According to the invention compounds which, unlike the so-called adhesion promoters or coupling reagents, contain only groups reacting with the particle surface but no polyreactive groups such as radically polymerizable groups, e.g. (meth)acryl, (meth)acrylamide, vinyl, vinyl ether or epoxide groups which enter into a covalent bond with the resin matrix (A) are particularly suitable. Such compounds are called non-polymerizable surface modifiers here. These compounds have the advantage that a stable bond does not form between the ceramic particle surface and the polymer matrix in the cured green body, which simplifies the complete removal of the polymer portions in the debinding process.

Linear or branched carboxylic acids, such as e.g. formic acid, acetic acid, propionic acid, octanoic acid, isobutyric acid, isovaleric acid, pivalic acid, acid phosphoric acid esters such as e.g. dimethyl, diethyl, dipropyl, dibutyl, dipentyl, dihexyl, dioctyl or di(2-ethylhexyl)phosphate, or phosphonic acids, e.g. such as methyl, ethyl, propyl, butyl, hexyl, octyl- or phenylphosphonic acid are particularly suitable as non-polymerizable surface modifiers. Silanes suitable as non-polymerizable surface modifiers are for example propyltrimethoxysilane, phenyltrimethoxysilane, hexyltrimethoxysilane, octyltrimethoxysilane, trimethylchlorosilane, trimethylbromosilane, trimethylmethoxysilane or hexamethyldisilazane.

According to a preferred embodiment, the slips according to the invention contain an inhibitor to prevent a spontaneous polyreaction as stabilizer as component D. The inhibitors or stabilizers improve the storage stability of the slips and also prevent an uncontrolled polyreaction in the stereolithographic tank. The inhibitors are preferably added in such a quantity that the slips are storage-stable over a period of approx. 2-3 years. The inhibitors are particularly preferably used in a quantity of 0.001 to 1.0 wt.-%, quite particularly preferably 0.001 to 0.50 wt.-%, in each case relative to the overall mass of the slip.

Phenols such as hydroquinone monomethyl ether (MEHQ) or 2,6-di-tert-butyl-4-methyl-phenol (BHT), which are really effective only in the presence of oxygen and are preferably used in a concentration range from 200-2000 ppm are used as so-called aerobic inhibitors for radical reaction resins and thiol-ene resins. Suitable anaerobic inhibitors are phenothiazine, 2,2,6,6-tetramethyl-piperidine-1-oxyl radical (TEMPO), iodine and copper-(I)-iodide. These act even at low concentrations of preferably 10-50 ppm also in the absence of oxygen. A polymerization does not then take place until these additives are consumed. It is advantageous to use a mixture of aerobic and anaerobic inhibitors. Basic alkaline and alkaline earth salts of saturated and unsaturated carboxylic acid, for example sodium methylate, calcium stearate or lithium oleate, can advantageously be used as inhibitors for cationic polymerization. On the other hand, the Michael reaction can be inhibited by acids, for example by acetic acid or p-toluenesulphonic acid.

Aerobic inhibitors are preferably used in a quantity of 0.01 to 0.50 wt.-% and anaerobic inhibitors in a quantity of 0.001 to 0.02 wt.-%, each relative to the overall mass of the slip. Preferred mixtures contain 0.01-0.10 wt.-% aerobic inhibitors and 0.001 to 0.01 wt.-% anaerobic inhibitors, likewise relative to the overall mass of the slip.

According to a further preferred embodiment of the invention, the slips contain a so-called debinding accelerator as component E. The latter is preferably used in a quantity of 0 to 20 wt.-%, particularly preferably 0.01 to 10 wt.-%, in each case relative to the overall mass of the slip. By debinding accelerators are meant substances which facilitate the removal of the binder during the debinding process.

The debinding of the green compact can be promoted or influenced in targeted manner by suitable, i.e. polyreaction effective substances in the polyreaction resin. On the one hand, these are additives which influence the network formation, such as in particular chain-transfer-active substances, so-called chain transfer agents, which result in a reduction in the polymer network density and thus in a better thermal decomposability. Known chain transfer agents e.g. for the radical polymerization are in particular mercaptans, such as e.g. lauryl mercaptan, and disulphides. Disulphides, in particular dithiourethane disulphides, such as e.g. tetramethylthiuram disulphide or isopropylxanthogenic acid disulphide act as so-called photoiniferters in radical photopolymerization. They are compounds which both act as photoinitiators (photoini-) and participate in transfer reactions (-fer-) and termination reactions (-ter) (cf. T. Ostsu, M. Yoshida, *Makromol. Chem., Rapid. Commun.* 3 (1982) 127-132: Role of Initiator-Transfer Agent-Terminator (Iniferter) in Radical Polymerizations: Polymer Design by Organic Disulfides as Iniferters, which is hereby incorporated by reference in its entirety). The addition of chain-transfer-active substances, i.e. chain transfer agents or photoiniferters, effects a reduction of the network density of the polyreaction network with an almost unchanged reactivity of the polyreaction resin mixture. Chain transfer agents and photoiniferters are preferably used in a quantity of 0.005 to 2 wt.-% and particularly preferably 0.1 to 1.0 wt.-%, relative to component (A).

According to the invention, comonomers which lead to a reduction in the thermal stability of polymer networks can also advantageously be used as debinding accelerators. Comonomers which contain thermally labile groups, such as e.g. peroxide, azo or urethane groups, which are incorporated into the polymer network during the stereolithographic process and then accelerate the degradation of the polymer network in the thermal debinding process are suitable for this. A preferred example of a polymerizable peroxide is 4,4'-divinyl benzoyl peroxide which can be obtained by reaction of 4-vinyl benzoyl chloride with sodium peroxide. A preferred example of a polymerizable azo compound is the ester of 2-hydroxyethyl methacrylate and 4,4'-azobis-(4-cyanovaleric acid). Preferred thermally labile urethanes can be obtained from diisocyanates, for example by reaction of 2,2, 4-trimethylhexamethylene diisocyanate (TMDI) or toluylene diisocyanate (TDI) with hydroxypropyl acrylate (HPA) or 2-hydroxyethyl acrylate (HEA). A further example of a thermally labile monomer building block is represented by $\alpha,\alpha,\alpha',\alpha'$-tetramethyl-1,4-benzene-dimethyl acrylate, the incorporation of which into a Michael addition network for example of diacrylates and diacetoacetates in the presence of catalytic acid quantities leads to an accelerated decomposition of the polymer network.

Moreover comonomers the polyreaction products of which are readily thermally degradable are suitable as debinding accelerators. Comonomers which like $\alpha$-methylstyrene have a low ceiling temperature $T_c$ are preferred for radical polymerization resins. The ceiling temperature is the limit temperature at which the polymerization is in equilibrium with the depolymerization and can be calculated from the quotient of the polymerization enthalpy and the polymerization entropy (cf. H.-G. Elias, *Makromoleküle*, Vol. 1, 6th ed., Wiley-VCH, Weinheim etc. 1999, 193 et. seq., which is hereby incorporated by reference in its entirety). For example, for $\alpha$-methylstyrene $T_c$ is 61° C. The ceiling temperature $T_c$ of polytetrahydrofuran (PTHF) is 80° C. Accordingly, the decomposability of poly(meth)acrylate networks can be accelerated e.g. by using telechels, in particular PTHF di(meth)acrylate telechels as comonomer. According to the invention, comonomers with a ceiling temperature of –10 to 150° C., preferably 10 to 150° C. and particularly preferably 20 to 130° C. are particularly suitable. The comonomers are preferably used in a quantity of 0.1 to 30 wt.-% and particularly preferably 0.5 to 20 wt.-%, relative to component (A).

The separate or joint use of the abovenamed chain transfer agents, photoiniferters and comonomers to improve the debinding of ceramic or glass ceramic green compacts is likewise a subject of the invention.

The slips according to the invention preferably contain a chromophoric component as component F. The chromophoric component is preferably used in a quantity of 0.00001 to 2.0 wt.-% and particularly preferably 0.001 to 1.0 wt.-%, and quite particularly preferably 0.01 to 0.5 wt.-%, relative to the mass of component C.

The customary colorants or pigments are not suitable according to the invention as chromophoric component, as they are not stable enough to survive the debinding or sintering process. According to the invention, reactive transition metal compounds which on the one hand are soluble in binder A and do not adversely affect the course of the photocuring and which on the other hand form chromophoric transition metal ions during the debinding of the stereolithographically prepared ceramic green compact or the sintering of the ceramic white body obtained therefrom are used as component F. Transition metal compounds preferred as chromophoric component are in particular acetylacetonates or carboxylic acid salts of the elements iron, cerium, praseodymium, terbium, lanthanum, tungsten, osmium, terbium and manganese. The salts of carboxylic acids, acetic, propionic, butyric, 2-ethylhexylcarboxylic, stearic and palmitic acid are preferred. Above all the corresponding Fe, Pr, Mn and Tb compounds such as e.g. iron (III) acetate or acetyl acetonate, manganese (III) acetate or acetyl acetonate, praseodymium (III) acetate or acetyl acetonate or terbium (III) acetate or acetyl acetonate and also the corresponding carboxylic acid salts are particularly preferred.

The chromophoric components are preferably chosen such that tooth-coloured ceramic spacers are obtained after the debinding and sintering.

The separate or joint use of the abovenamed transition metal compounds to colour ceramic mouldings and in particular to colour sintered ceramic mouldings, in particular the use as chromophoric component in RP processes for the preparation of ceramic mouldings and in particular for the preparation of sintered ceramic mouldings is likewise a subject of the invention.

According to the invention, accordingly slips are preferred which, in addition to the components A, B and C, contain an inhibitor D, a debinding accelerator E and/or a chromophoric component F. Particularly preferred are slips which contain the components A, B, C and D; A, B, C and E; A, B, C and F, quite particularly preferred are slips which contain the components A, B, C, D and E; A, B, C, D and F; A, B, C, E and F, and in particular slips which contain the components A, B, C, D, E and F. It is preferred in each case to use the above-defined components and preferred components, preferably in the named quantities.

In addition to the components A to F, the slips according to the invention can contain further components as additives.

Although according to the invention the use of customary polymeric dispersants can be dispensed with in order to achieve a high solids content, because the thickening action of the ceramic particles is markedly reduced as a result of the surface modification with the monomeric, non-polymerizable surface modifiers, the slips can also contain one or more dispersants which further prevent the formation of agglomerates and the settling of the ceramic particles. Preferred dispersants for aqueous slips are above all polymers, in particular polyelectrolytes, e.g. polycarboxylic acids or polycarboxylic acid salts, or non-ionic polymers, such as e.g. polyethylene glycol or carboxymethylcellulose. Polyelectrolytes which, like e.g. ammonium polycarboxylate, carry ionic groups and which therefore adsorb relatively easily on the surface of solids, e.g. on ceramic particles, are suitable as dispersants for aqueous slips. The polyelectrolyte ions can then give the particles an electric charge, which is then referred to as an electrosteric effect. The dispersant action of the polyelectrolytes depends i.a. on their concentration, the type and degree of coverage of the particles, the pH of the solution and its ionic strength. In the case of organic, non-aqueous slips, polymers which are soluble in the polyreaction resin, such as for example poly(meth)acrylates which are soluble in light-cured (meth)acrylate resins, are particularly suitable as dispersants. Dispersants are optionally used in a quantity of preferably 0.5 to 3 wt.-% relative to the mass of the slip. Dispersants with a molar mass in the range from 500 to 5,000 g/mol are preferred.

The particles of component C can already be pre-treated with dispersants before the slip is produced. If this treatment takes place before the surface modification, the particles are only treated with a relatively small quantity of dispersant, preferably a maximum of 1 wt.-%, in order to avoid an inhibition of the surface modification. If the particles are treated with dispersant after the surface modification, the proportion of dispersant is preferably 0.1 to 5 wt.-%, in each case relative to the mass of the particles.

The ceramic slips according to the invention can contain one or more plasticizers as further components. The plasticizer(s) can optionally prevent the ceramic green body from becoming brittle after the photochemical curing and a possible drying. Plasticizers also ensure a sufficient flexibility of the stereolithographically produced green body. Preferred plasticizers are phthalates, such as e.g. dibutyl or dihexyl phthalate, non-acid phosphates, such as e.g. tributyl or tricresyl phosphate, n-octanol, glycerol or polyethylene glycols. Plasticizers are preferably used in a quantity of 0 to 15 wt.-% and particularly preferably 0.1 to 5 wt.-%, relative to the mass of component (A).

Furthermore, the slips according to the invention can also advantageously contain a solvent. The compounds named above as plasticizers are suitable as solvents for example.

Components which have a boiling point of at least approx. 120° C., preferably from 150 to 250° C., particularly preferably from 180 to 230° C., are preferably used as solvents with the result that a stereolithographic processing of the slip does not result in an early evaporation. Mixtures of solvents which can be progressively evaporated in a temperature range between 150 and 250° C. are particularly suitable. Quite particularly suitable are octanol, triethylene glycol divinyl ether, 2-amino-2-methyl-1-propanol, 2-methyl-2,4-pentanediol, ammonium citrate tribasic (solid), tripropylene glycol, tetraethylene glycol, triethylene glycol, triethyl citrate, ethyl acetoacetate, cyclohexanol, cyclohexanone, diethylene glycol monomethyl ether, dibutyl oxalate, 2,5-dimethoxytetrahydrofuran, polyethylene glycol 300, 1- or 2-nonanol, diethylene glycol diethyl ether, 2,5-dimethoxytetrahydrofuran, dibutyl oxalate, cyclohexanol, cyclohexanone, ethyl acetoacetate and mixtures thereof.

It was found that the evaporation of the above solvents leads to the formation of micropores in the green body which then close again upon sintering but which also make possible and promote the escape of gases in the debinding step and thus prevent the formation of stresses and cracks. Moreover, the danger of a separation of the stereolithographically produced layers is reduced and a complete removal of the organic components favoured.

Solvent(s) are preferably used in a quantity of 5 to 50 wt.-%, particularly preferably from 10 to 30 wt.-%, relative to the mass of component (A).

Alternatively, a porosity of the green body can also be achieved by removing by extraction elutable portions before heat treatment. Suitable extractable components are water-soluble polymers such as e.g. polyvinyl alcohol, polyvinyl pyrrolidone and polyethylene glycols. Furthermore, benzine-soluble substances such as paraffins or waxes and long-chained fatty acid esters can be used. The preferred quantity of extractable components in the resin matrix is between 0 and 40 wt.-%, particularly preferably between 0.1 and 30 wt.-%, relative to component (A).

Furthermore, the slips according to the invention can contain components which promote the oxidative degradation of the polymer matrix during the debinding process, such as e.g. peroxides stable at room temperature, or also catalytic components which make possible a catalytic debinding. In addition to peroxides, other substances which have an oxidizing effect, such as e.g. nitric acid, or which split or form oxidants, are also suitable.

In addition, the slips according to the invention can contain defoaming and/or antiskinning agents which prevent foaming during the preparation of the slips or the formation of a skin during the processing of the slips. Defoaming and/or antiskinning agents are preferably used in each case in a quantity of 0 to 5 wt.-% and particularly preferably 0.1 to 2 wt.-% in the organic matrix, relative to the mass of component (A).

The rheological properties of the slips according to the invention are preferably set such that their viscosity lies in the range of from 200 mPa·s to 2,000 Pa·s, preferably 500 mPa·s to 500 Pa·s, more preferably 500 mPa·s to 50 Pa·s, most preferably 200 to 20000 mPa·s, and particularly preferably 500 to 5000 mPa·s. It is advantageous if there are no yield points if at all possible. The viscosity is determined at 23° C. with a plate-plate viscometer.

The slips according to the invention are particularly suitable for the preparation of ceramic or glass ceramic mouldings, in particular for the preparation of dental restorations, such as e.g. inlays, onlays, veneers, crowns, bridges or frameworks.

A subject of the invention is furthermore a process for the preparation of ceramic or glass ceramic mouldings in which
(a) a green body is prepared by curing a slip according to the invention by local introduction of radiation energy with formation of the geometric shape of the green body,
(b) the green body is then subjected to a heat treatment to remove the binder (debinding), in order to obtain a white body, and
(c) the white body is then sintered.

The preparation of the green body in step (a) takes place by rapid prototyping, preferably by stereolithography. A ceramic green body is prepared by layered radiation curing of a free-flowing ceramic slip which is debound in step (b). The binder used is removed by heating the green body to a temperature of preferably 90° C. to 600° C., and the so-called white body is obtained. The white body is sintered in step (c) to form a dense ceramic moulding. The sintering of the white body takes place in the sintering furnace, preferably at a temperature of 650 to 1100° C., preferably 700 to 900° C., for glass ceramic, 1100 to 1600° C., preferably 1400 to 1500° C., for zirconium dioxide, and 1400 to 1800° C., preferably 1600 to 1700° C., for aluminium oxide. The ceramic mouldings prepared according to the process according to the invention are characterized by a high strength and great detail accuracy. The bending strength according to ISO 6872 is more than 100 MPa, in particular in the range from 150 to 500 MPa, for mouldings made of glass ceramic. Mouldings made of $Al_2O_3$ have a bending strength of preferably more than 300 MPa, in particular in the range from 500 to 700 MPa and mouldings made of $ZrO_2$ over 500 MPa, in particular from 800 to 1100 MPa.

The invention is explained in more detail below by means of drawings and examples.

As FIG. 1 shows, the device comprises a container 1 for the slip 7 according to the invention. The container 1 is also called a polymerization tank or tank. In the embodiment shown, the tank 1 has a transparent window 2 through which the slip can be selectively illuminated and cured from below. Arranged underneath the tank 1 is a computer-controlled, movable mirror 3, a so-called micro-mirror array, which is irradiated with a radiation source 4. The image of the mirror 3 is projected onto the transparent window 2 by an optical device 5. Arranged above the tank 1 is a substrate carrier 6 movable in Z direction which carries the body 8 constructed in layers. The substrate carrier 6 can have a carrier plate, not shown here. The substrate carrier 6 is immersed in the slip until the distance between the carrier 6 or the body 8 attached thereto and the inner surface of the tank 1 corresponds to the layer thickness of the layer to be produced. The slip layer between carrier 6 and inner tank surface is then selectively illuminated and cured through the transparent window 2 with the help of the mirror 3. Cured areas form which adhere to the carrier 6. The carrier 6 is then raised in Z direction, with the result that a slip layer with the desired thickness forms again between the adhering layer and the inner tank surface. This layer is also selectively cured by renewed illumination and the desired moulding, preferably a dental restoration, is constructed in layers by repeating the process.

EXAMPLES

Example 1

Preparation of a ZrO₂ Slip and its Stereolithographic Processing to form a High-Strength, Tooth-Coloured Ceramic Testpiece The liquid components listed in Table 1 were introduced and the photoinitiator Irgacure 819 (Ciba) and the praseodymium acetoacetonate dissolved in them accompanied by stirring. The ZrO₂ powder 3Y TZP (Tosoh) containing 3 mol-% Y₂O₃ surface-modified with iso-butyric acid was then added portionwise in a Dispermat dissolver (VMA) at 15,000 rpm and dispersed for 30 min until a highly-filled ZrO₂ slip with a fill level of approx. 41 vol.-% formed which was satisfactorily processable by stereolithography.

TABLE 1

Composition of a stereolithographically processable ZrO₂ ceramic slip

| Component | wt.-% |
|---|---|
| Ethoxylated pentaerythritol tetraacrylate (EPTA) | 3.50 |
| Urethane diacrylate UDPA (comprising TMDI and HPA) | 3.50 |
| Irgacure 819 | 0.50 |
| Hexanediol diacrylate (HDA) | 3.00 |
| Dolacol D 1003 (Zschimmer&Schwarz) | 3.90 |
| 1-octanol | 1.50 |
| PEG-300 | 3.00 |
| ZrO₂ | 81.00 |
| Pr (III) acetylacetonate | 0.10 |

The slip was converted into cylindrical biaxial-strength testpieces (diameter 15 mm and height 2.2 mm) by means of the Perfactory (Envisiontec) stereolithography unit customary in the trade. The heat treatment of the testpieces took place in a Nabertherm sintering furnace with catalytic secondary burning in the following steps: 1$^{st}$ step (debinding): thermal treatment up to 500° C. with a heating-up rate of 1 K/min. Then a holding phase of 90 min at 500° C. 2$^{nd}$ step (sintering): heating to 1500° C. with a heating-up rate of 20 K/min and a holding time of 1 h at 1500° C. The cooling took place in the furnace within ca. 12 h. Tooth-coloured testpieces were obtained. The density of the testpieces was determined according to the buoyancy method after sintering, wherein a value of greater than 99% of the theoretical density was achieved. The biaxial strength was determined according to ISO standard 6872. An average value for the biaxial strength of 1110 MPa (for n=10 testpieces) was determined, which corresponds to the value of a high-strength ceramic.

Example 2

Preparation of a Tooth-Coloured Crown Based on the ZrO₂ Slips from Example 1

Based on the ZrO₂ slip from Example 1, a green compact was prepared in the shape of a tooth crown in the Perfactory stereolithography unit customary in the trade using an STL (Standard Transformation Language) data set, and then debound and sintered analogously to Example 1. A high-strength tooth-coloured tooth crown was obtained.

Example 3

Preparation of Further Ceramic or Glass Ceramic Slips which are Suitable for a Stereolithographic Processing for the Preparation of High-Strength, Tooth-Coloured Dental Mouldings Analogously to Example 1, the compositions of ceramic and glass ceramic slips listed in Table 2 were prepared which were easily debindable and processable by stereolithography to form high-strength, tooth-coloured dental ceramic and glass ceramic mouldings.

TABLE 2

Composition of stereolithographically processable ceramic and glass ceramic slips for the preparation of dental mouldings

| Component | A [wt.-%] | B [wt.-%] | C [wt.-%] | D [wt.-%] |
|---|---|---|---|---|
| EPTA | 4.00 | 4.00 | 4.00 | 7.00 |
| UDPA | 5.50 | — | 3.50 | 5.50 |
| Urethane diacrylate comprising TDI and HPA | — | 5.50 | — | — |
| Dibenzoyldiethylgermanium | 0.50 | — | — | — |
| Irgacure 819 | — | 0.80 | 0.50 | 0.50 |
| HDA | 3.00 | 2.50 | 3.00 | 3.00 |
| Tetramethylthiuram disulphide | — | 0.20 | — | — |
| Byk-9077 | 2.00 | — | 1.00 | 2.00 |
| ZrO₂ (propionic acid-modified) | 80.00 | 80.00 | — | — |
| Aluminium oxide CT 300 SDT | — | — | 80.00 | — |
| GM cutting ceramic (type 595579) | — | — | — | 75.00 |
| 1-octanol | 1.90 | 3.90 | 4.80 | 3.80 |
| PEG-300 | 3.00 | 3.00 | 3.00 | 3.00 |
| Pr (III) acetylacetonate | 0.10 | — | 0.10 | 0.10 |
| Terbium (III) acetylacetonate | — | 0.10 | 0.10 | 0.10 |

Although various embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A light-curing slip composition for stereolithographic preparation of ceramic or glass ceramic materials comprising:
    (A) 5-65 wt.-% polymerization or polyaddition polyreactive binder,
    (B) 0.001-1.0 wt.-% photoinitiator, and
    (C) 35-90 wt.-% surface-modified ceramic particles and/or surface-modified glass ceramic particles,
    in each case relative to the overall mass of the slip; and
    (E) 0.01-20 wt.-% chain transfer agent debinding accelerator,
    relative to the mass of component A.

2. The slip according to claim 1, further comprising:
    0.001-1.0 wt-% inhibitor
    relative to the overall mass of the slip.

3. The slip according to claim 1, further comprising:
    0.00001-2.0 wt.-% chromophoric components,
    relative to the mass of component (C).

4. The slip according to claim 3, which contains a transition metal compound, as chromophoric component (F).

5. The slip according to claim 1, wherein the polyreactive binder (A) is selected from light-curing radically or cationically polymerizable resins, monomers for ring-opening metathesis polymerization, thiol-ene resins or Michael reaction resins.

6. The slip according to claim 1, wherein the glass ceramic particles or ceramic particles comprise pure $ZrO_2$, pure $Al_2O_3$, pure $ZrO_2$—$Al_2O_3$, $ZrO_2$ which is stabilized with $HfO_2$, CaO, $Y_2O_3$, $CeO_2$ and/or MgO, or $ZrO_2$—$Al_2O_3$ which is stabilized with $HfO_2$, CaO, $Y_2O_3$, $CeO_2$ and/or MgO, as component (C).

7. The slip according to claim 1, in which the particles of component (C) are surface-modified with a linear or branched carboxylic acid, an acid phosphoric acid ester, a phosphonic acid, or a silane, wherein the surface-modification agent does not contain a radically polymerizable group.

8. The slip according to claim 7, in which the particles of component (C) are surface-modified with (i) formic acid, acetic acid, propionic acid, octanoic acid, isobutyric acid, isovaleric acid or pivalic acid; (ii) dimethyl, diethyl, dipropyl, dibutyl, dipentyl, dihexyl, dioctyl or di(2-ethylhexyl)phosphate; (iii) methyl, ethyl, propyl, butyl, hexyl, octyl- or phenylphosphonic acid; or (iv) propyltrimethoxysilane, phenyltrimethoxysilane, hexyltrimethoxysilane, octyltrimethoxysilane, trimethylchlorosilane, trimethylbromosilane, trimethylmethoxysilane or hexamethyldisilazane, wherein the surface-modification agent does not contain a radically polymerizable group.

9. The slip according to claim 1, in which the particles of component (C) have a particle size in the range from 50 nm to 50 μm.

10. The slip according to claim 1, further comprising a solvent.

11. The slip according to claim 10, wherein the solvent comprises phthalates, dibutyl or dihexyl phthalate, non-acid phosphates, tributyl or tricresyl phosphate, n-octanol, glycerol, polyethylene glycols, octanol, triethylene glycol divinyl ether, 2-amino-2-methyl-1-propanol, 2-methyl-2,4-pentanediol, ammonium citrate tribasic (solid), tripropylene glycol, tetraethylene glycol, triethylene glycol, triethyl citrate, ethyl acetoacetate, cyclohexanol, cyclohexanone, diethylene glycol monomethyl ether, dibutyl oxalate, 2,5-dimethoxytetrahydrofuran, polyethylene glycol 300, 1- or 2-nonanol, diethylene glycol diethyl ether, 2,5-dimethoxytetrahydrofuran, dibutyl oxalate, cyclohexanol, cyclohexanone, ethyl acetoacetate or mixtures thereof.

12. The slip according to claim 1, wherein the chain transfer agent is a mercaptan, a disulphide or a photoiniferter.

13. The slip according to claim 12, wherein the chain transfer agent is lauryl mercaptan, a dithiourethane disulphide, tetramethylthiuram disulphide or isopropylxanthogenic acid disulphide.

14. The slip according to claim 1, wherein the debinding accelerator is a comonomer which has one or more thermally labile groups; or a comonomer with a temperature at which the polymerization is in equilibrium with the depolymerization (ceiling temperature) of from −10 to 150° C.; or a telechel with radically polymerizable groups.

15. The slip according to claim 14, wherein the one or more thermal labile groups, comprises one or more peroxide, azo or urethane groups.

16. The slip according to claim 14, wherein the comonomers with a ceiling temperature from −10 to 150° C. comprise α-methylstyrene or polytetrahydrofuran (PTHF).

17. The slip according to claim 14, wherein the telechel with radically polymerizable groups comprises PTHF-di(meth)acrylate telechel.

18. A light-curing slip composition for stereolithographic preparation of ceramic or glass ceramic materials comprising:
(A) 5-65 wt.-% polymerization or polyaddition polyreactive binder,
(B) 0.001-1.0 wt.-% photoinitiator and
(C) 35-90 wt.-% surface-modified ceramic particles and/or surface-modified glass ceramic particles,
in each case relative to the overall mass of the slip, which has a viscosity in the range of from 200 mPa·s to 2,000 Pa·s.

19. The slip according to claim 18, wherein the polyreactive binder (A) is selected from light-curing radically or cationically polymerizable resins, monomers for ring-opening metathesis polymerization, thiol-ene resins or Michael reaction resins.

20. The slip according to claim 18, wherein the glass ceramic particles or ceramic particles comprise pure $ZrO_2$, pure $Al_2O_3$, pure $ZrO_2$—$Al_2O_3$, $ZrO_2$ which is stabilized with $HfO_2$, CaO, $Y_2O_3$, $CeO_2$ and/or MgO, or $ZrO_2$—$Al_2O_3$ which is stabilized with $HfO_2$, CaO, $Y_2O_3$, $CeO_2$ and/or MgO, as component (C).

21. The slip according to claim 18, in which the particles of component (C) are surface-modified with a linear or branched carboxylic acid, an acid phosphoric acid ester, a phosphonic acid, or a silane, wherein the surface-modification agent does not contain a radically polymerizable group.

22. The slip according to claim 21, in which the particles of component (C) are surface-modified with (i) formic acid, acetic acid, propionic acid, octanoic acid, isobutyric acid, isovaleric acid or pivalic acid; (ii) dimethyl, diethyl, dipropyl, dibutyl, dipentyl, dihexyl, dioctyl or di(2-ethylhexyl)phosphate; (iii) methyl, ethyl, propyl, butyl, hexyl, octyl- or phenylphosphonic acid; or (iv) propyltrimethoxysilane, phenyltrimethoxysilane, hexyltrimethoxysilane, octyltrimethoxysilane, trimethylchlorosilane, trimethylbromosilane, trimethylmethoxysilane or hexamethyldisilazane, wherein the surface-modification agent does not contain a radically polymerizable group.

23. The slip according to claim 18, in which the particles of component (C) have a particle size in the range from 50 nm to 50 μm.

24. The slip according to claim 18, further comprising:
(D) 0.001-1.0 wt-% inhibitor
relative to the overall mass of the slip.

25. The slip according to claim 18, further comprising:
(E) 0-20 wt-% debinding accelerator
relative to the mass of component A.

26. The slip according to claim 25, wherein the debinding accelerator is a chain transfer agent.

27. The slip according to claim 26, wherein the chain transfer agent is a mercaptan, a disulphide or a photoiniferter.

28. The slip according to claim 27, wherein the chain transfer agent is lauryl mercaptan, a dithiourethane disulphide, tetramethylthiuram disulphide or isopropylxanthogenic acid disulphide.

29. The slip according to claim 25, wherein the debinding accelerator is a comonomer which has one or more thermally labile groups; or a comonomer with a temperature at which the polymerization is in equilibrium with the depolymerization (ceiling temperature) of from −10 to 150° C.; or a telechel with radically polymerizable groups.

30. The slip according to claim 29, wherein the one or more thermal labile groups, comprises one or more peroxide, azo or urethane groups.

31. The slip according to claim 29, wherein the comonomers with a ceiling temperature from −10 to 150° C. comprise α-methylstyrene or polytetrahydrofuran (PTHF).

32. The slip according to claim 29, wherein the telechel with radically polymerizable groups comprises PTHF-di(meth)acrylate telechel.

33. The slip according to claim 18, further comprising:
(F) 0.00001-2.0 wt.-% chromophoric components,
relative to the mass of component (C).

34. The slip according to claim 33, which contains a transition metal compound, as chromophoric component (F).

35. The slip according to claim 34, which contains an acetyl acetonate or a carboxylic acid salt of the elements iron, cerium, praseodymium, terbium, lanthanum, tungsten, osmium, terbium or manganese; or iron (III) acetate or iron (III) acetyl acetonate, manganese (III) acetate or manganese (III) acetyl acetonate, praseodymium (III) acetate or praseodymium (III) acetyl acetonate or terbium (III) acetate or terbium (III) acetyl acetonate transition metal compound as chromophoric component.

36. The slip according to claim 18, further comprising a solvent.

37. The slip according to claim 36, wherein the solvent comprises phthalates, dibutyl or dihexyl phthalate, non-acid phosphates, tributyl or tricresyl phosphate, n-octanol, glycerol, polyethylene glycols, octanol, triethylene glycol divinyl ether, 2-amino-2-methyl-1-propanol, 2-methyl-2,4-pentanediol, ammonium citrate tribasic (solid), tripropylene glycol, tetraethylene glycol, triethylene glycol, triethyl citrate, ethyl acetoacetate, cyclohexanol, cyclohexanone, diethylene glycol monomethyl ether, dibutyl oxalate, 2,5-dimethoxytetrahydrofuran, polyethylene glycol 300, 1- or 2-nonanol, diethylene glycol diethyl ether, 2,5-dimethoxytetrahydrofuran, dibutyl oxalate, cyclohexanol, cyclohexanone, ethyl acetoacetate or mixtures thereof.

38. A light-curing slip composition for stereo lithographic preparation of ceramic or glass ceramic materials comprising:
(A) 5-65 wt.-% polymerization or polyaddition polyreactive binder,
(B) 0.001-1.0 wt.-% photoinitiator and
(C) 35-90 wt.-% surface-modified ceramic particles and/or surface-modified glass ceramic particles,
in each case relative to the overall mass of the slip; and
(F) 0.00001-2.0 wt.-% chromophoric components,
relative to the mass of component (C) which contains an acetyl acetonate or a carboxylic acid salt of the elements iron, cerium, praseodymium, terbium, lanthanum, tungsten, osmium, terbium or manganese; or iron (III) acetate or iron (III) acetyl acetonate, manganese (III) acetate or manganese (III) acetyl acetonate, praseodymium (III) acetate or praseodymium (III) acetyl acetonate or terbium (III) acetate or terbium (III) acetyl acetonate transition metal compound as chromophoric component.

39. The slip according to claim 38, wherein the polyreactive binder (A) is selected from light-curing radically or cationically polymerizable resins, monomers for ring-opening metathesis polymerization, thiol-ene resins or Michael reaction resins.

40. The slip according to claim 38, wherein the glass ceramic particles or ceramic particles comprise pure $ZrO_2$, pure $Al_2O_3$, pure $ZrO_2$—$Al_2O_3$, $ZrO_2$ which is stabilized with $HfO_2$, CaO, $Y_2O_3$, $CeO_2$ and/or MgO, or $ZrO_2$—$Al_2O_3$ which is stabilized with $HfO_2$, CaO, $Y_2O_3$, $CeO_2$ and/or MgO, as component (C).

41. The slip according to claim 38, in which the particles of component (C) are surface-modified with a linear or branched carboxylic acid, an acid phosphoric acid ester, a phosphonic acid, or a silane, wherein the surface-modification agent does not contain a radically polymerizable group.

42. The slip according to claim 41, in which the particles of component (C) are surface-modified with (i) formic acid, acetic acid, propionic acid, octanoic acid, isobutyric acid, isovaleric acid or pivalic acid; (ii) dimethyl, diethyl, dipropyl, dibutyl, dipentyl, dihexyl, dioctyl or di(2-ethylhexyl)phosphate; (iii) methyl, ethyl, propyl, butyl, hexyl, octyl- or phenylphosphonic acid; or (iv) propyltrimethoxysilane, phenyltrimethoxysilane, hexyltrimethoxysilane, octyltrimethoxysilane, trimethylchlorosilane, trimethylbromosilane, trimethylmethoxysilane or hexamethyldisilazane, wherein the surface-modification agent does not contain a radically polymerizable group.

43. The slip according to claim 38, in which the particles of component (C) have a particle size in the range from 50 nm to 50 μm.

44. The slip according to claim 38, further comprising:
(D) 0.001-1.0 wt-% inhibitor
relative to the overall mass of the slip.

45. The slip according to claim 38, further comprising:
(E) 0-20 wt-% debinding accelerator
relative to the mass of component A.

46. The slip according to claim 45, wherein the debinding accelerator is a chain transfer agent.

47. The slip according to claim 46, wherein the chain transfer agent is a mercaptan, a disulphide or a photoiniferter.

48. The slip according to claim 47, wherein the chain transfer agent is lauryl mercaptan, a dithiourethane disulphide, tetramethylthiuram disulphide or isopropylxanthogenic acid disulphide.

49. The slip according to claim 45, wherein the debinding accelerator is a comonomer which has one or more thermally labile groups; or a comonomer with a temperature at which the polymerization is in equilibrium with the depolymerization (ceiling temperature) of from −10 to 150° C.; or a telechel with radically polymerizable groups.

50. The slip according to claim 49, wherein the one or more thermal labile groups, comprises one or more peroxide, azo or urethane groups.

51. The slip according to claim 49, wherein the comonomers with a ceiling temperature from −10 to 150° C. comprise α-methylstyrene or polytetrahydrofuran (PTHF).

52. The slip according to claim 49, wherein the telechel with radically polymerizable groups comprises PTHF-di (meth)acrylate telechel.

53. The slip according to claim 38, further comprising a solvent.

54. The slip according to claim 53, wherein the solvent comprises phthalates, dibutyl or dihexyl phthalate, non-acid phosphates, tributyl or tricresyl phosphate, n-octanol, glycerol, polyethylene glycols, octanol, triethylene glycol divinyl ether, 2-amino-2-methyl-1-propanol, 2-methyl-2,4-pentanediol, ammonium citrate tribasic (solid), tripropylene glycol, tetraethylene glycol, triethylene glycol, triethyl citrate, ethyl acetoacetate, cyclohexanol, cyclohexanone, diethylene glycol monomethyl ether, dibutyl oxalate, 2,5-dimethoxytetrahydrofuran, polyethylene glycol 300, 1- or 2-nonanol, diethylene glycol diethyl ether, 2,5-dimethoxytetrahydrofuran, dibutyl oxalate, cyclohexanol, cyclohexanone, ethyl acetoacetate or mixtures thereof.

55. A method for the preparation of ceramic or glass ceramic mouldings comprising layered radiation curing of the slip composition according to claim 1.

56. Method according to claim 55, wherein the ceramic moulding is a dental restoration, an inlay, onlay, veneer, a crown, bridge or a framework.

57. A Process for the preparation of a ceramic or glass ceramic moulding comprising:
(a) preparing a green body by curing a slip composition according to claim 1 by local introduction of radiation energy with formation of the geometric shape of the green body,
(b) then subjecting the green body to a debinding heat treatment to remove the binder, in order to obtain a white body, and
(c) sintering the white body.

* * * * *